(12) United States Patent
Hwang et al.

(10) Patent No.: US 11,984,235 B2
(45) Date of Patent: May 14, 2024

(54) SHUTTER MECHANISM

(71) Applicant: Canon U.S.A., Inc., Melville, NY (US)

(72) Inventors: Charles George Hwang, Wellesley, MA (US); James Hastings Houskeeper, Mendon, MA (US)

(73) Assignee: Canon U.S.A., Inc., Melville, NY (US)

( * ) Notice: Subject to any disclaimer, the term of this patent is extended or adjusted under 35 U.S.C. 154(b) by 315 days.

(21) Appl. No.: 17/502,675

(22) Filed: Oct. 15, 2021

(65) Prior Publication Data
US 2023/0123224 A1 Apr. 20, 2023

(51) Int. Cl.
G21K 1/04 (2006.01)
A61B 6/00 (2006.01)
G01N 23/04 (2018.01)

(52) U.S. Cl.
CPC .............. G21K 1/04 (2013.01); G01N 23/04 (2013.01); A61B 6/542 (2013.01)

(58) Field of Classification Search
CPC .......... G21K 1/04; G01N 23/04; A61B 6/542; A61B 6/405; A61B 6/06
See application file for complete search history.

(56) References Cited

U.S. PATENT DOCUMENTS

| 2,593,526 A | 4/1952 | Bell |
| 3,048,700 A | 8/1962 | Koerner |
| 3,287,561 A | 11/1966 | Ingles |
| 7,983,388 B2* | 7/2011 | Michaelsen .............. G21K 1/04 378/150 |

FOREIGN PATENT DOCUMENTS

| JP | 4965841 B2 | 7/2012 |
| WO | 2011022769 A1 | 3/2011 |

OTHER PUBLICATIONS

M. A. Hill et al., The Development of Technology for Effective Respiratory-Gated Irradiation Using an Image-Guided Small Animal Irradiator, Radiation Research, 188(3):247-263, Jul. 2017.

* cited by examiner

Primary Examiner — Courtney D Thomas
(74) Attorney, Agent, or Firm — Canon U.S.A., Inc. IP Division

(57) ABSTRACT

Some embodiments of a device comprise a shuttle member, wherein the shuttle member includes a body, wherein the body includes an opening that extends through the body, and wherein at least part of the shuttle is radiopaque; a first actuator; and a second actuator, wherein the first actuator and the second actuator are positioned on opposite sides of the shuttle member, wherein the first actuator is configured to move the shuttle member in a first direction, and wherein the second actuator is configured to move the shuttle member in a second direction that is opposite to the first direction.

20 Claims, 9 Drawing Sheets

SHUTTER MECHANISM

BACKGROUND

Technical Field

This application generally concerns shutter mechanisms, including shutter mechanisms that are used in X-ray radiography.

Background

Radiography (e.g., medical radiography, industrial radiography) can generate images of the internal structures of objects. For example, to create an image of an object in X-ray radiography, a beam of X-rays is generated by an X-ray generator and is projected toward the object. Some of the X-rays are absorbed by the object, depending on the object's density and structural composition, and some of the X-rays pass through the object. The X-rays that have passed through the object are detected by a detector.

A shutter controls the irradiation or illumination of the object by selectively blocking or allowing the transmission of beams of electromagnetic radiation (e.g., beams of X-rays, beams of visible light). When open, the shutter allows the transmission of beams of electromagnetic radiation. When closed, the shutter blocks the transmission of beams of electromagnetic radiation.

SUMMARY

Some embodiments of a shutter device comprise a shuttle member, wherein the shuttle member includes a body, wherein the body includes an opening that extends through the body, and wherein at least part of the shuttle is radiopaque; a first actuator; and a second actuator, wherein the first actuator and the second actuator are positioned on opposite sides of the shuttle member, wherein the first actuator is configured to move the shuttle member in a first direction, and wherein the second actuator is configured to move the shuttle member in a second direction that is opposite to the first direction.

Some embodiments of a device comprise an aperture; a shuttle member, wherein the shuttle member includes a body, wherein the shuttle member includes an opening that extends through the body, and wherein the shuttle member includes a radiopaque portion; a first actuator; and a second actuator, wherein the first actuator is configured to move the shuttle member to a first location in which the opening that extends through the body is aligned with the aperture, and wherein the second actuator is configured to move the shuttle member to a second location in which the radiopaque portion is aligned with the aperture.

Some embodiments of a shuttle device comprise a body, wherein at least a part of the body is radiopaque, an opening that extends through the body, a first end that is configured to be held by a first actuator, and a second end that is configured to be held by a second actuator.

DESCRIPTION

Figure 1A:
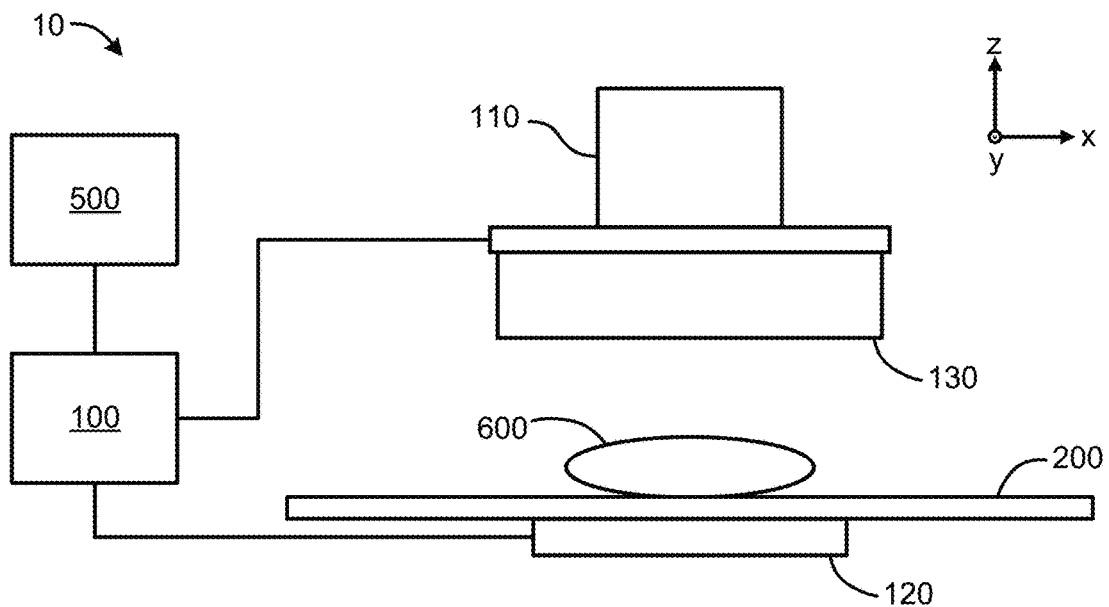
FIG. 1A is a schematic of an example embodiment of an X-ray radiography system.

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein. Furthermore, some embodiments include features from two or more of the following explanatory embodiments.

Also, as used herein, the conjunction "or" generally refers to an inclusive "or," although "or" may refer to an exclusive "or" if expressly indicated or if the context indicates that the "or" must be an exclusive "or." Furthermore, as used herein, the terms "first," "second," and so on, do not necessarily denote any ordinal, sequential, or priority relation, but are used to more clearly distinguish one member, operation, element, or set from another, unless specified otherwise.

And, in the following description and in the drawings, like reference numerals designate identical or corresponding members throughout the several views.

FIG. 1A is a schematic of an example embodiment of an X-ray radiography system 10. The system 10 includes one or more computers 100, an X-ray generator 110, an X-ray detector 120, a beam-control device 130, a support surface 200, and a display device 500. When active, the X-ray generator 110 emits X-rays toward the beam-control device 130. The beam-control device 130 controls the X-ray beams that travel through the beam-control device 130 toward an object 600, the support surface 200, and the X-ray detector 120. The X-rays that pass through the object 600 and the support surface 200 are detected by the X-ray detector 120, which generates signals based on the detected X-rays and transmits the signals to the one or more computers 100. The one or more computers 100 generate one or more images of the object 600 based on the signals, and the one or more computers 100 send the one or more images to the display device 500, which displays the images.

Figure 1B:
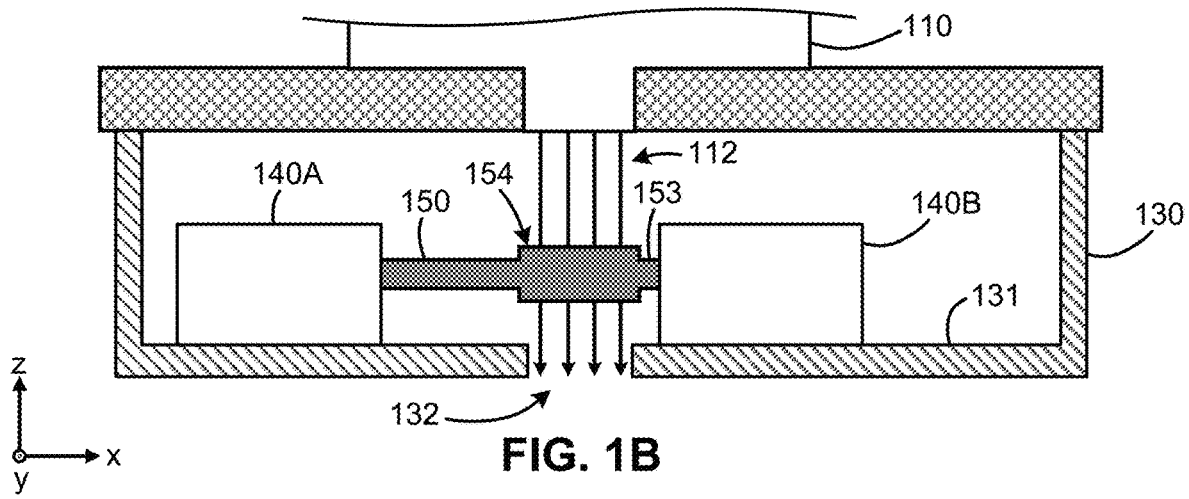
FIGS. 1B-C illustrate a cutaway view of an example embodiment of a beam-control device.
Figure 1C:
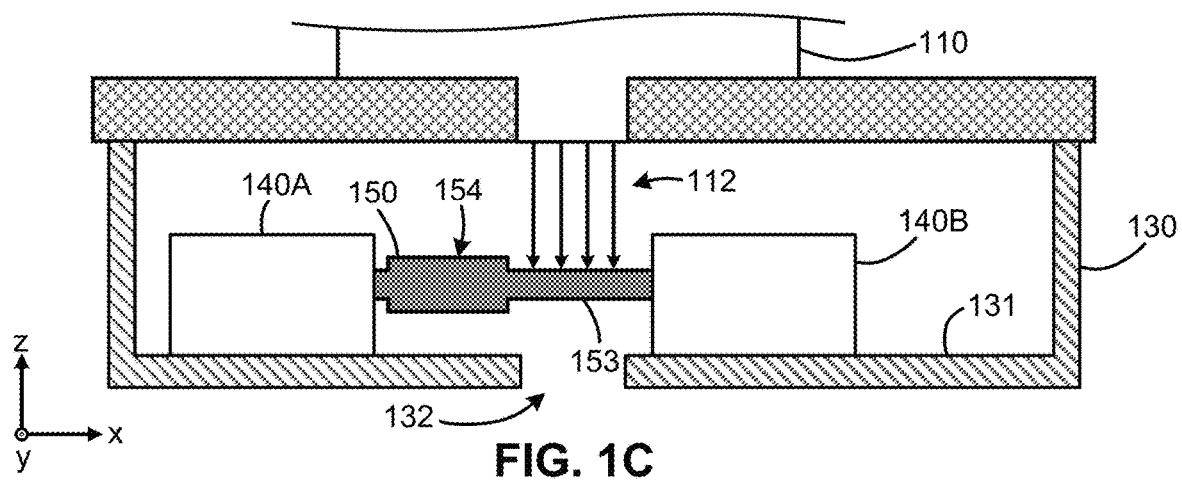

FIGS. 1B-C illustrate a cutaway view of an example embodiment of a beam-control device 130. FIGS. 1B-C illustrate the beam-control device from a view that is parallel to the y axis (and perpendicular to the x and z axes). This embodiment of a beam-control device 130 includes a shuttle member 150, actuators 140A-B, and an aperture 132. Also, some embodiments of the beam-control device 130 include other components, for example a collimator. In this embodiment, the actuators 140A-B are fixed to an inner lower surface 131 of the beam-control device 130.

The actuators 140A-B hold and move the shuttle member 150. In this embodiment, the actuators 140A-B are positioned on opposite sides of the shuttle member 150. Thus, a first actuator 140A is positioned on one side of the shuttle member 150, and a second actuator 140B is positioned on an opposite side of the shuttle member 150. The actuators 140A-B can move the shuttle member 150 (along the x-axis in FIGS. 1B-C) between an open position and a closed position. Thus, the actuators 140A-B and the shuttle member 150 may constitute a shutter mechanism.

Examples of actuators 140A-B include the following: pneumatic actuators, magnetic actuators, hydraulic actuators, electromechanical actuators (e.g., electrical-motor-and-cam actuators, linear-motor actuators), and electrohydraulic actuators. Thus, some types of actuators (e.g., magnetic actuators) exert a pulling force on the shuttle member 150 and some types of actuators (e.g., pneumatic actuators) exert a pushing force on the shuttle member 150.

The two actuators 140A-B may be the same type of actuator, or they may be different types of actuators. For example, the first actuator 140A may be a magnetic actuator, and the second actuator 140B may be a pneumatic actuator. Also for example, the first actuator 140A may be an electromechanical actuator, and the second actuator 140B may be a pneumatic actuator.

And one of the actuators 140A-B in FIGS. 1B-C may be replaced with a spring. The spring can exert either a pushing force or a pulling force on the shuttle member 150, depending on the actuator that is used with the spring. For example, in the embodiment shown in FIGS. 1B-C, if the second actuator 140B is replaced with a spring and the first actuator 140A is a type of actuator that exerts a pushing force on the shuttle member 150, then the spring exerts a pushing force on the shuttle member 150. And, in the embodiment shown in FIGS. 1B-C, if the second actuator 140B is replaced with a spring and the first actuator 140A is a type of actuator that exerts a pulling force on the shuttle member 150, then the spring exerts a pulling force on the shuttle member 150.

In the open position, which is shown in FIG. 1B, the shuttle member 150 allows X-ray beams 112 to travel through a window 154 of the shuttle member 150, and through the aperture 132, to the object 600 and the X-ray detector 120. In the closed position, which is shown in FIG. 1C, an opaque portion 153 of the shuttle member 150 blocks the X-ray beams 112, and thus the X-ray beams 112 cannot travel through the aperture 132 to the object 600 and to the X-ray detector 120.

Figure 2A:
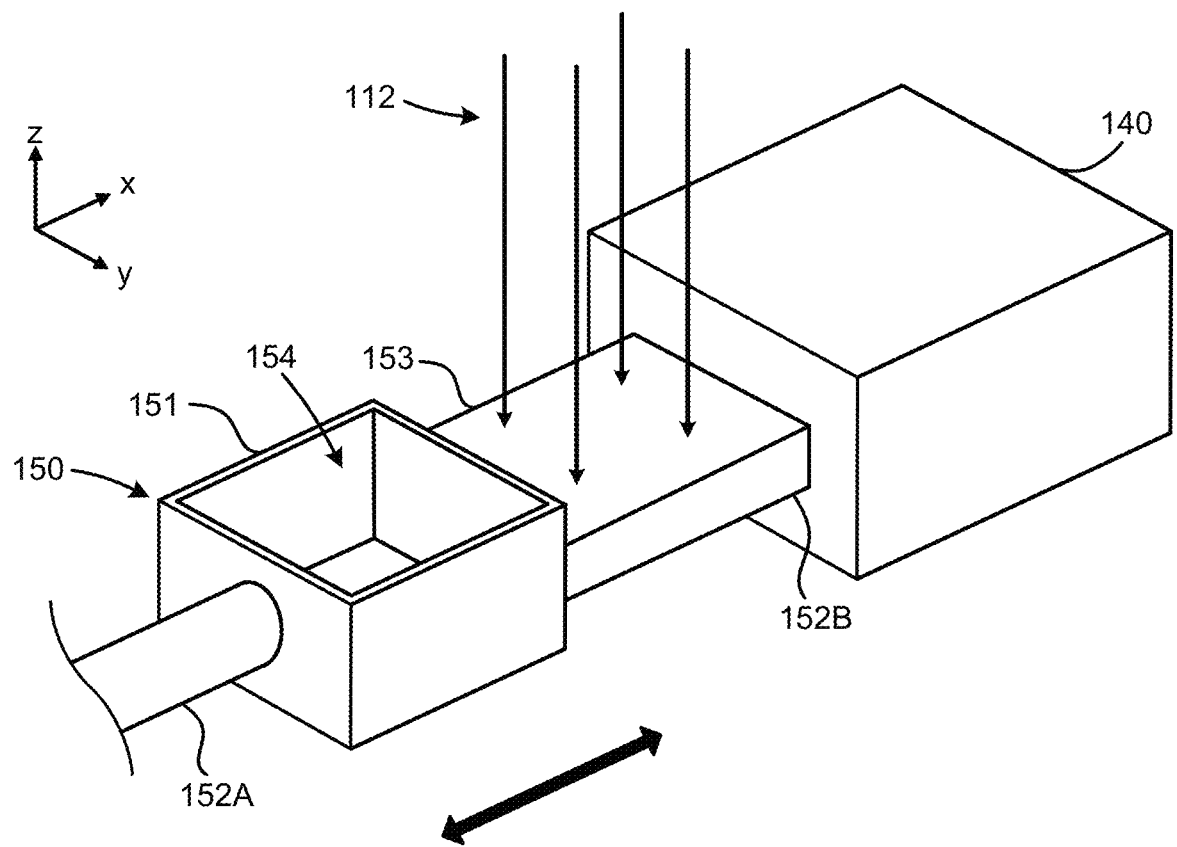
FIGS. 2A-B illustrate a perspective view of an example embodiment of a shuttle member and an actuator.
Figure 2B:
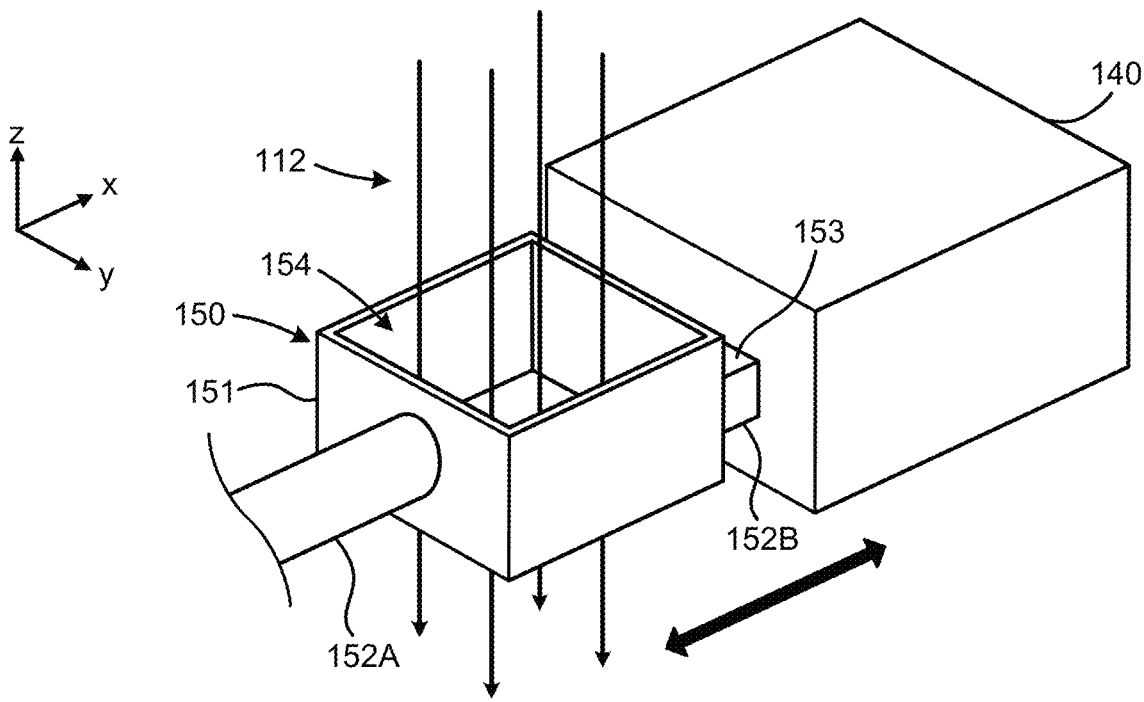

FIGS. 2A-B illustrate a perspective view of an example embodiment of a shuttle member 150 and an actuator 140 (another actuator is omitted to make more of the shuttle member 150 visible). The shuttle member 150 includes a body 151 and two arms 152A-B. A first arm 152A is held by the actuator that is not illustrated in FIGS. 2A-B. A second arm 152B is held by the actuator 140 that is shown in FIGS. 2A-B. The body 151 includes an opaque (e.g., radiopaque or radiodense) portion 153 and a window 154 (an opening that extends through the body of the shuttle member 150). The shuttle member 150 can be moved back and forth along the x axis by the actuators. In FIG. 2A, the shuttle member 150 is in the closed position. In the closed position, the opaque portion 153 is positioned between the X-ray beams 112 (or other beams of electromagnetic radiation) that are emitted by the X-ray generator 110 (or other generator of electromagnetic radiation) and an aperture, and the opaque portion 153 blocks the X-ray beams 112 from traveling through the aperture. In FIG. 2B, the shuttle member 150 is in the open position. In the open position, the window 154 is positioned between the X-ray beams that are emitted by the X-ray generator 110 and the aperture, and the window 154 allows the X-ray beams 112 to travel through the shuttle member 150 to the aperture.

The entire shuttle member 150 may be composed of the same radiopaque (radiodense) material. And different members of the shuttle member 150 may be composed of different materials. For example, the opaque portion 153 may be composed of a more radiopaque or radiodense material (e.g., a ferromagnetic metal, such as steel (for example stainless steel)), and the arms 152A-B and the window 154 may be composed of a less radiopaque or radiodense material.

Figure 3A:
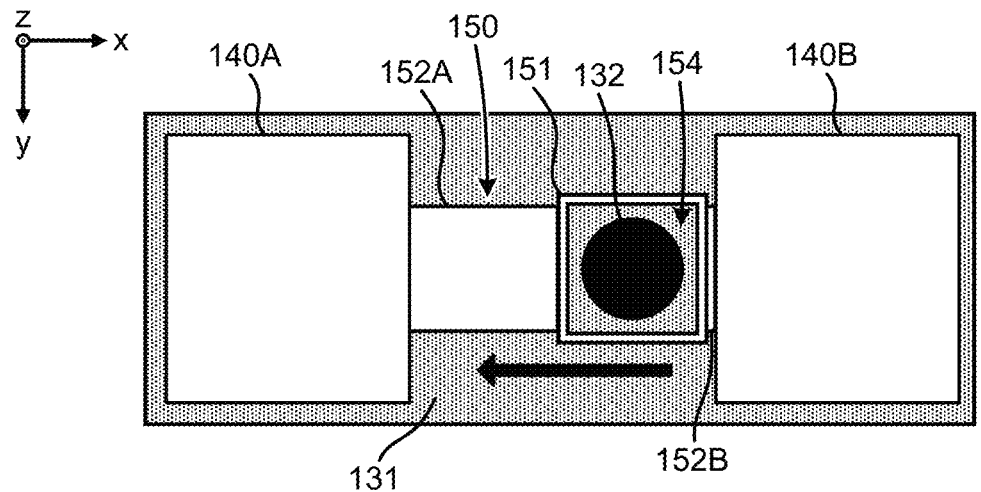
FIGS. 3A-C illustrate different positions of an example embodiment of a shuttle member and two actuators.
Figure 3B:
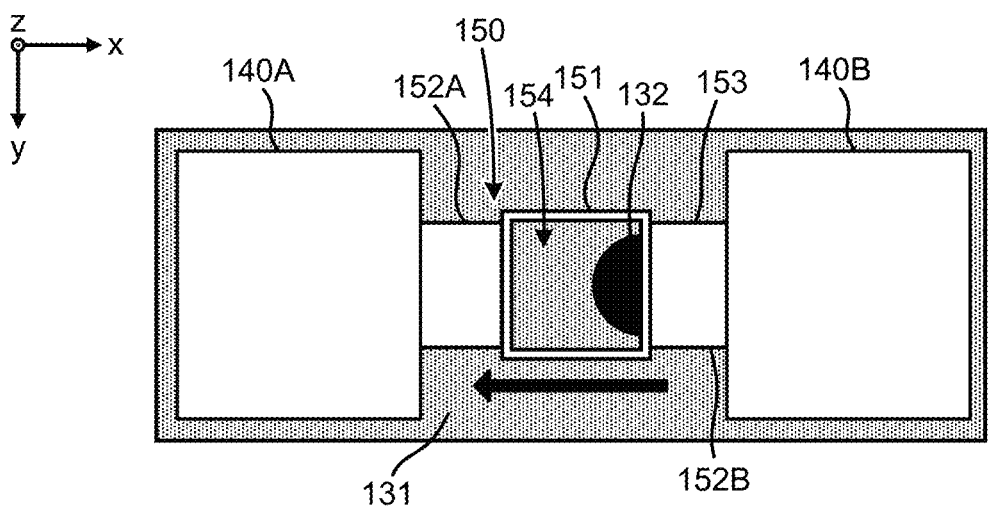
Figure 3C:
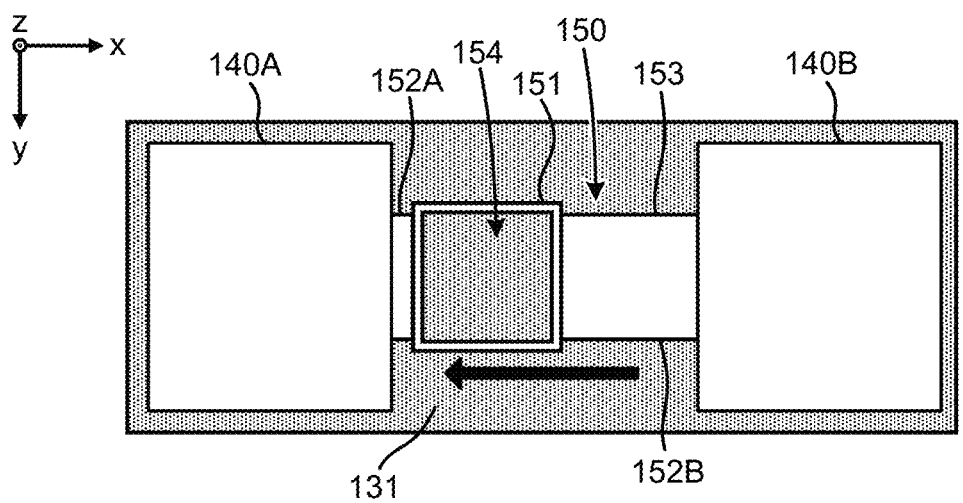

FIGS. 3A-C illustrate different positions of an example embodiment of a shuttle member and two actuators. Also, FIGS. 3A-C illustrate the shuttle member 150 and the actuators 140A-B from a view that is parallel to the z axis (and perpendicular to both the x and y axes).

FIG. 3A shows the shuttle member 150 in an open position, FIG. 3B shows the shuttle member 150 in a partially open (and partially closed) position, and FIG. 3C shows the shuttle member in a closed position.

The actuators 140A-B move the shuttle member 150, along the x axis, from the open position (FIG. 3A) to the partially open position (FIG. 3B), and then from the partially open position (FIG. 3B) to the closed position (FIG. 3C). Also, the actuators 140A-B may move the shuttle member 150 in the opposite direction (i.e., from the closed position to the partially open position, and from the partially open position to the open position). In the open position, the aperture 132 is aligned with (and visible through) the window 154. Thus, in the open position, the window 154 can allow beams of electromagnetic radiation to travel through the window 154 and through the aperture 132. In the partially open position, only part of the aperture 132 is aligned with (and visible through) the window 154, and the remainder of the aperture 132 is blocked by the opaque portion 153. And, in the closed position, the opaque portion 153 blocks the entire aperture 132.

The actuators 140A-B may rapidly move the shuttle member 150 from the open position to the closed position and vice versa. Also, when the shuttle member 150 is moving, only one of the actuators 140A-B may be activated, and thus only one of the actuators 140A-B may exert a force on the shuttle member 150 while the shuttle member 150 is moving. For example, if the actuators 140A-B are both a type of actuator that exerts a pushing force, then, when the shuttle member 150 is moving from the open position (in FIG. 3A) to the closed position (in FIG. 3C), only the second actuator 140B may be active and exerting a force on the shuttle member 150. And, when the shuttle member 150 is moving from the closed position (in FIG. 3C) to the open position (in FIG. 3A), only the first actuator 140A may be active and exerting a force on the shuttle member 150.

Also for example, if the actuators 140A-B are both a type of actuator that exerts a pulling force, then, while the shuttle member 150 is moving from the open position (in FIG. 3A) to the closed position (in FIG. 3C), only the first actuator 140A may be active and exerting a force on the shuttle member 150. And, while the shuttle member 150 is moving from the closed position (in FIG. 3C) to the open position (in FIG. 3A), only the second actuator 140B may be active and exerting a force on the shuttle member 150.

Consequently, in some embodiments, the actuators 140A-B are alternatingly activated to move the shuttle member 150 back and forth between the open position and the closed position.

Also, both actuators 140A-B may be active at the same time with their power levels set such that the actuator that moves the shuttle member 150 in the desired direction exerts more force on the shuttle member 150 than the other actuator.

The two actuators 140A-B may move the shuttle member 150 very rapidly in both directions. This can allow the shuttle member 150 to quickly move between the open position and the closed position, which may minimize the amount of electromagnetic radiation that travels through the aperture. This can be especially advantageous in radiographic imaging, where exposure to ionizing radiation can be harmful to a patient, by limiting the expose to only what is necessary for imaging.

And the two actuators 140A-B and the shuttle member 150 may form a shutter mechanism that is simpler, cheaper, and has fewer parts than other shutter mechanisms, such as an iris pedal-type of shutter.

Different embodiments of the shuttle member 150 have various shapes. For example, FIGS. 4A-G illustrate example embodiments of shuttle members 150.

Figure 4A:
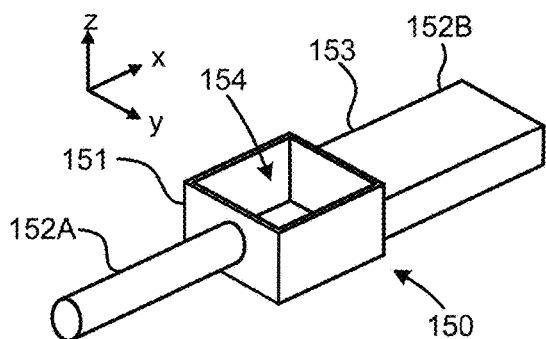
FIGS. 4A-G illustrate example embodiments of shuttle members.

The shuttle member 150 in FIG. 4A includes two arms 152A-B that are narrower than the body 151, which includes a window 154 and an opaque portion 153. The arms 152A-B may include structures (e.g., notches, grooves, pegs, and ridges) that cooperate with corresponding structures of the actuators to prevent the shuttle member 150 from rotating relative to the actuators.

Figure 4B:
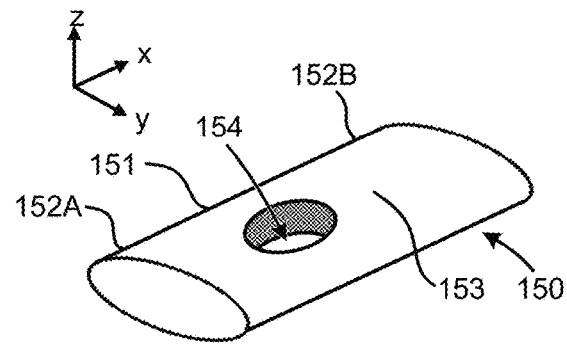

The shuttle member 150 in FIG. 4B has an elliptical cross section. Also, the arms 152A-B blend in with the contour of the body 151, which includes a window 154 and an opaque portion 153. And, in this embodiment, the window 154 is circular or elliptical.

Figure 4C:
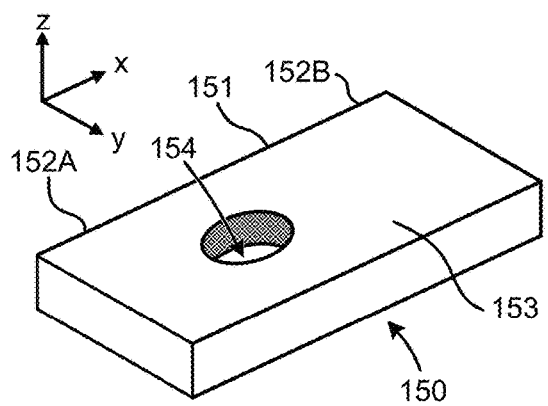

The shuttle member 150 in FIG. 4C has a rectangular cross section. Also, the arms 152A-B blend in with the contour the body 151, which includes a window 154 and an opaque portion 153. And, in this embodiment, the window 154 is circular or elliptical.

Figure 4D:
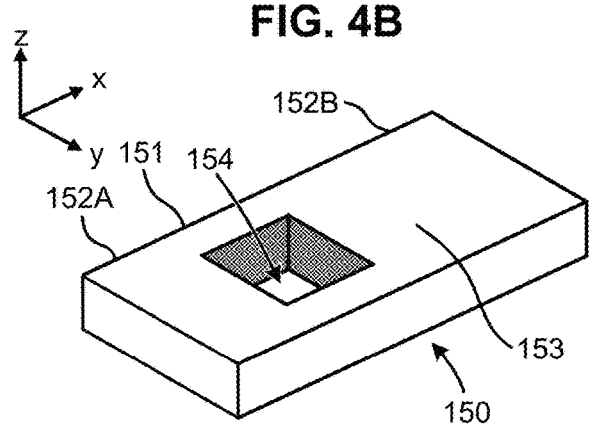

The shuttle member 150 in FIG. 4D has a rectangular cross section. Additionally, the arms 152A-B blend in with the contour the body 151, which includes a window 154 and an opaque portion 153. And, in this embodiment, the window 154 is square or rectangular.

Figure 4E:
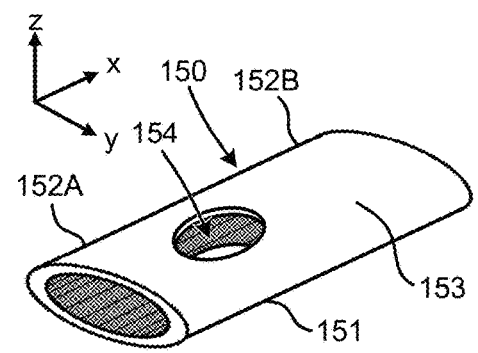

The shuttle member 150 in FIG. 4E has an elliptical cross section. Also, the arms 152A-B blend in with the contour the body 151, which includes a window 154 and an opaque portion 153. And, in this embodiment, the window 154 is circular or elliptical. Furthermore, the shuttle member 150 is hollow along its longitudinal axis.

Figure 4F:
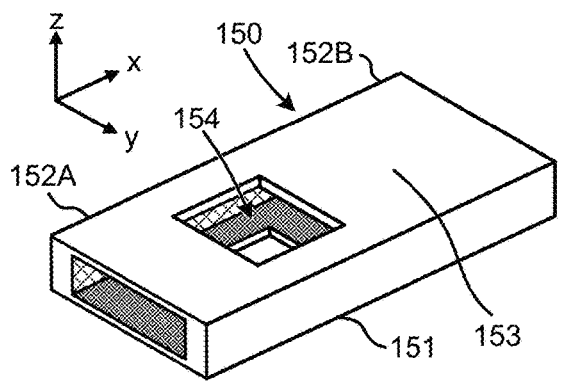

The shuttle member 150 in FIG. 4F has a rectangular cross section. Also, the arms 152A-B blend in with the contour the body 151, which includes a window 154 and an opaque portion 153. And, in this embodiment, the window 154 is square or rectangular. Like FIG. 4E, the shuttle member 150 is hollow along its longitudinal axis.

A hollow shuttle member 150 (e.g., as illustrated in FIGS. 4E-F) may have less mass and, thus, using the same applied force, the actuators can move (e.g., accelerate) a less-massive shuttle member 150 more quickly.

Figure 4G:
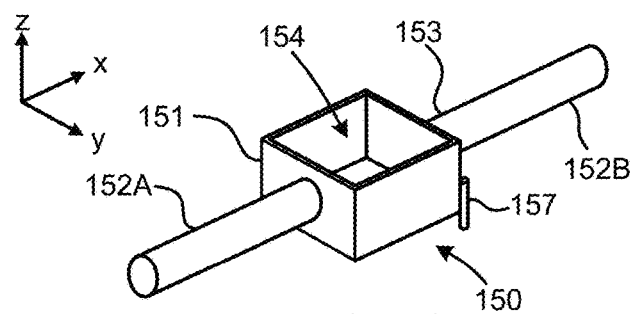

The shuttle member 150 in FIG. 4G includes two arms 152A-B that are narrower than the body 151, which includes a window 154. One of the arms (152B) includes an opaque portion 153. The shuttle member 150 also includes a peg 157. The peg 157 prevents the shuttle member 150 from rotating relative to the actuators or relative to the beam-control device 130. The peg 157 travels in a groove, channel, or slot in the beam-control device 130 (e.g., a groove, channel, or slot in the inner lower surface 131 of the beam-control device 130).

Furthermore, some embodiments of the shuttle member have cross sections that have other shapes, such as triangles, pentagons, and octagons, for example.

Figure 5A:
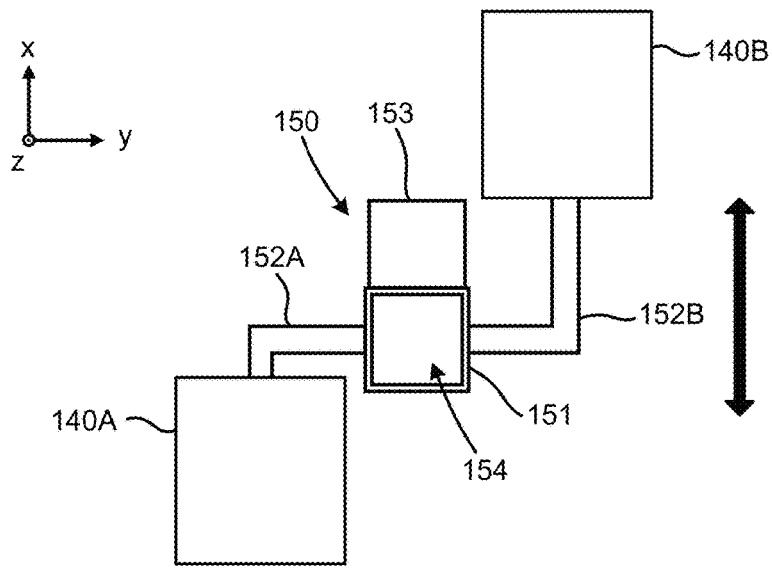
FIGS. 5A-C illustrate example embodiments of shuttle members and actuators.
Figure 5B:
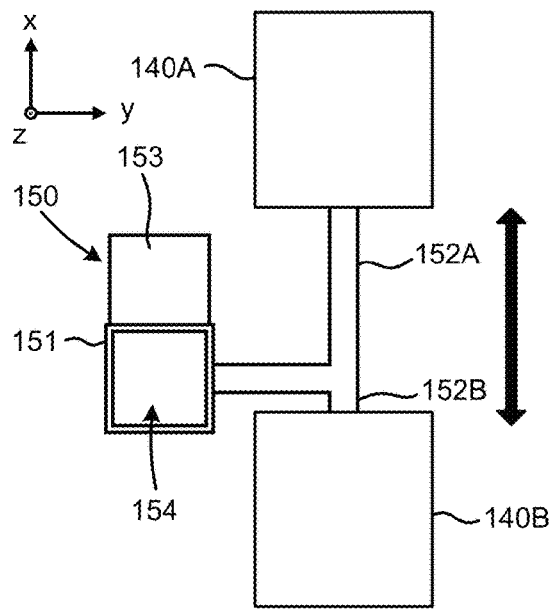
Figure 5C:
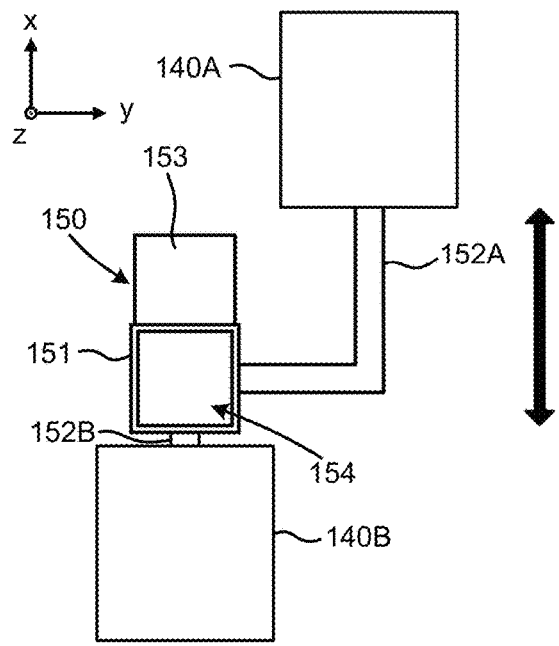

FIGS. 5A-C illustrate example embodiments of shuttle members and actuators. As shown by the embodiment in FIG. 5A, the window 154 and the opaque portion 153 of the shuttle member 150 and both of the actuators 140A-B may not be aligned along the axis on which the shuttle member 150 moves (which is the x axis in FIG. 5A). Accordingly, the shuttle member 150 and one or both of the actuators 140A-B may be horizontally offset (have different positions on the y axis in FIG. 5A).

As shown by the embodiment in FIG. 5B, the window 154 and the opaque portion 153 may be horizontally offset (have different positions on they axis in FIG. 5B) from the two actuators 140A-B.

As shown by the embodiment in FIG. 5C, one of the actuators 140A may be horizontally offset (have different positions on the y axis in FIG. 5B) from the other actuator 140B, the window 154, and the opaque portion 153.

Figure 6A:
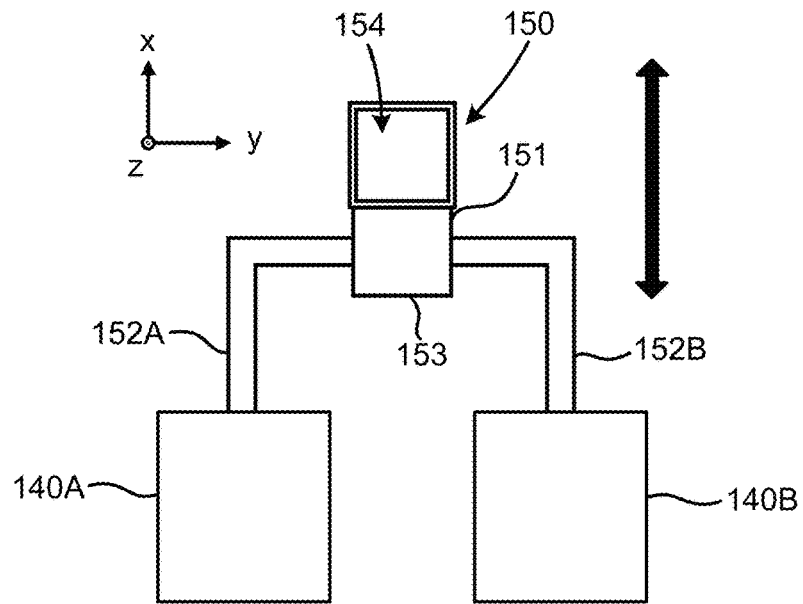
FIGS. 6A-C illustrate example embodiments of shuttle members and actuators.
Figure 6B:
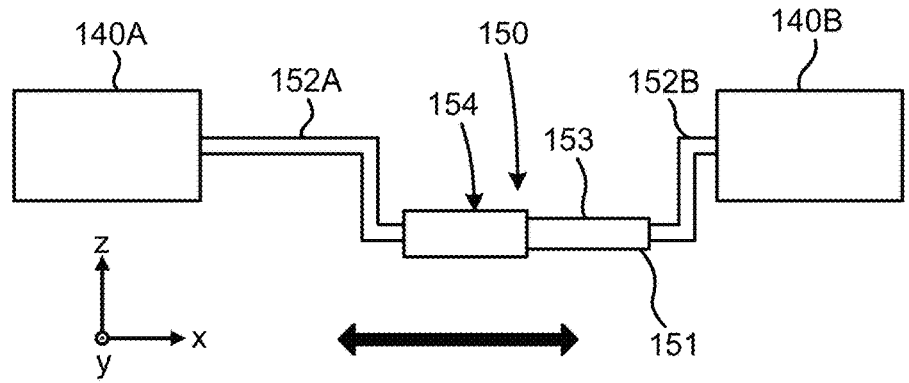
Figure 6C:
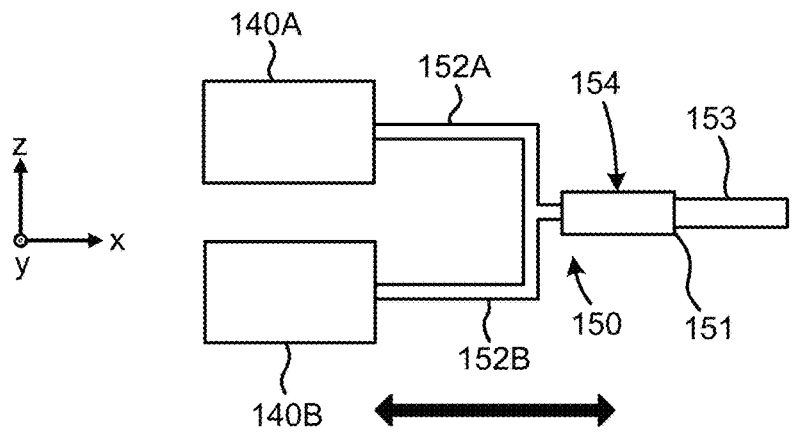

FIGS. 6A-C illustrate example embodiments of shuttle members and actuators. In the embodiment shown in FIG. 6A, one of the actuators 140A-B exerts a pushing force on the shuttle member 150, and the other one of the actuators 140A-B exerts a pulling force on the shuttle member 150. Thus, both of the actuators 140A-B may be on the same side of the shuttle member 150 (the same side of a y-z plane that passes through the window 154 or through the opaque portion 153).

As shown by FIG. 6B, in some embodiments the actuators 140A-B are vertically offset (offset along the z axis in FIG. 6B) from the window 154 and the opaque portion 153.

As shown by FIG. 6C, in some embodiments the actuators 140A-B are vertically offset (offset along the z axis in FIG. 6C) from the window 154 and the opaque portion 153 and are vertically offset from each other. Additionally, in the embodiment shown in FIG. 6C, one of the actuators 140A-B exerts a pushing force on the shuttle member 150, and the other one of the actuators 140A-B exerts a pulling force on the shuttle member 150. Thus, in FIG. 6C, both of the actuators 140A-B are on the same side of the shuttle member 150 (the same side of a y-z plane that passes through the window 154 or through the opaque portion 153).

Figure 7A:
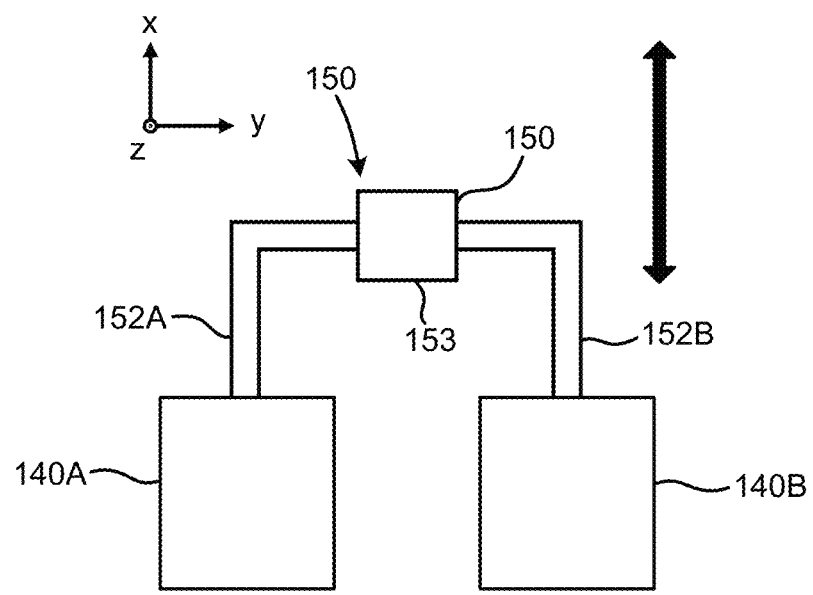
FIGS. 7A-B illustrate example embodiments of shuttle members and actuators.
Figure 7B:
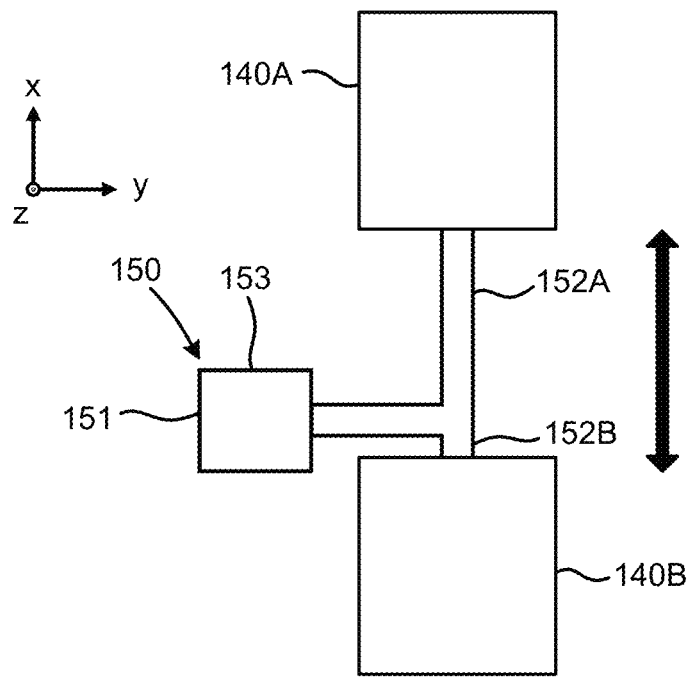

FIGS. 7A-B illustrate example embodiments of shuttle members and actuators. In FIG. 7A, the body 151 of the shuttle member 150 does not include a window. Also, one of the actuators 140A-B exerts a pushing force on the shuttle member 150, and the other one of the actuators 140A-B exerts a pulling force on the shuttle member 150. Thus, when the shuttle member 150 is in the open position, the opaque portion 153 does not block the aperture, and the beams of light do not pass through a window in the shuttle member 150 as they travel to an aperture.

In FIG. 7B, the body 151 of the shuttle member 150 also does not include a window. Thus, when the shuttle member 150 is in the open position, the opaque portion 153 does not block the aperture, and the beams of light do not pass through a window in the shuttle member 150 as they travel to an aperture.

Figure 8A:
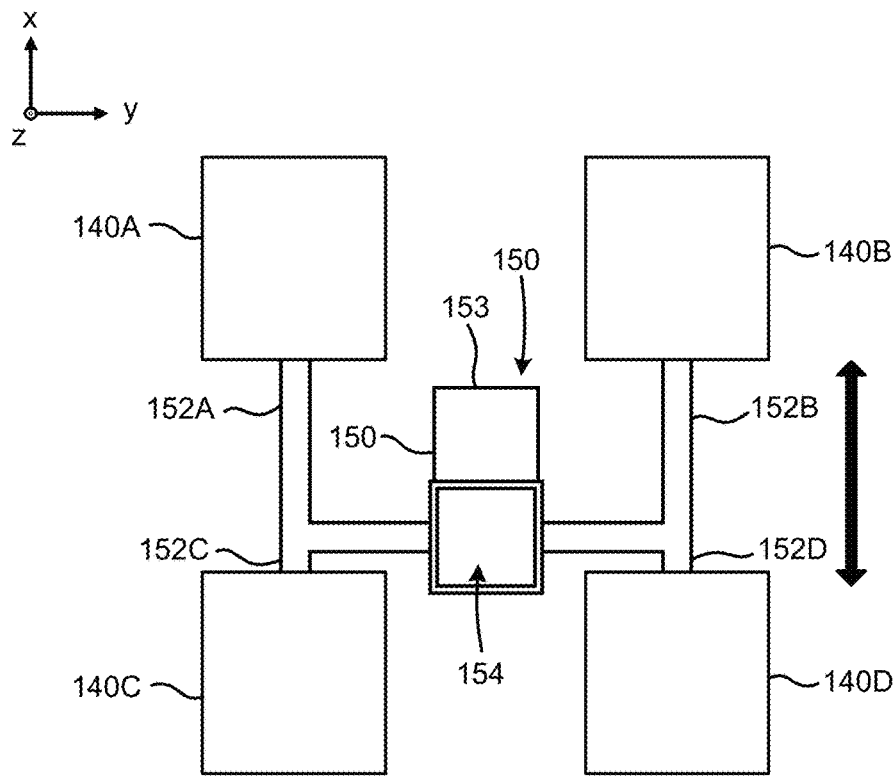
FIG. 8A illustrates an example embodiment of a shuttle member and actuators.

FIG. 8A illustrates an example embodiment of a shuttle member and actuators. As illustrated by this embodiment, which includes four actuators 140A-D, some embodiments have more than two actuators. The shuttle member 150 includes four arms 152A-D, each of which is held by a respective one of the four actuators 140A-D. The four actuators 140A-D may be able to move the shuttle member 150 between the open and closed positions more quickly than embodiments that use fewer actuators.

Figure 8B:
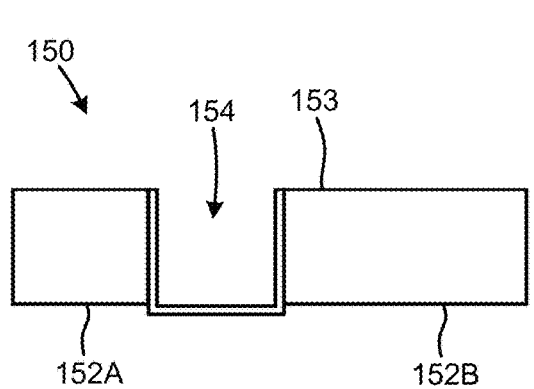
FIG. 8B illustrates an example embodiment of a shuttle member.

FIG. 8B illustrates an example embodiment of a shuttle member. The body 151 of the shuttle member 150 includes a window 154, but the perimeter of the window 154 is not entirely surrounded by the body 151.

Figure 8C:
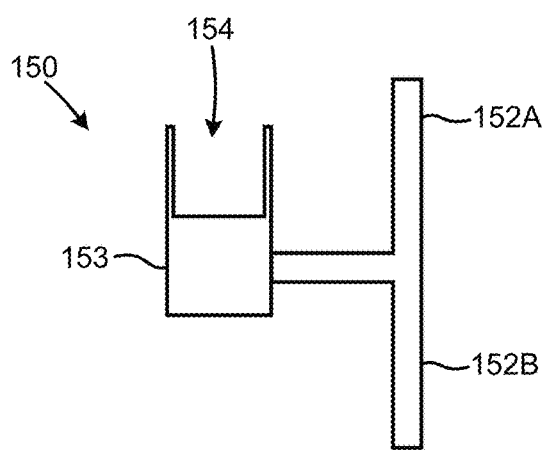
FIG. 8C illustrates an example embodiment of a shuttle member.

FIG. 8C illustrates an example embodiment of a shuttle member. The body 151 of the shuttle member 150 includes a window 154, but the perimeter of the window 154 is not entirely surrounded by the body 151.

Figure 9A:
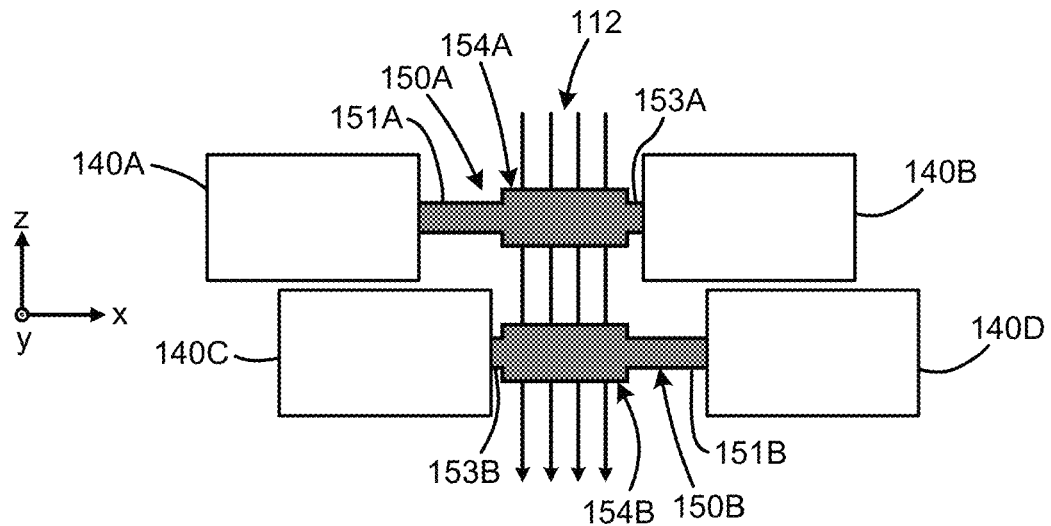
FIGS. 9A-B illustrate an example embodiment of two shuttle members and their respective actuators.
Figure 9B:
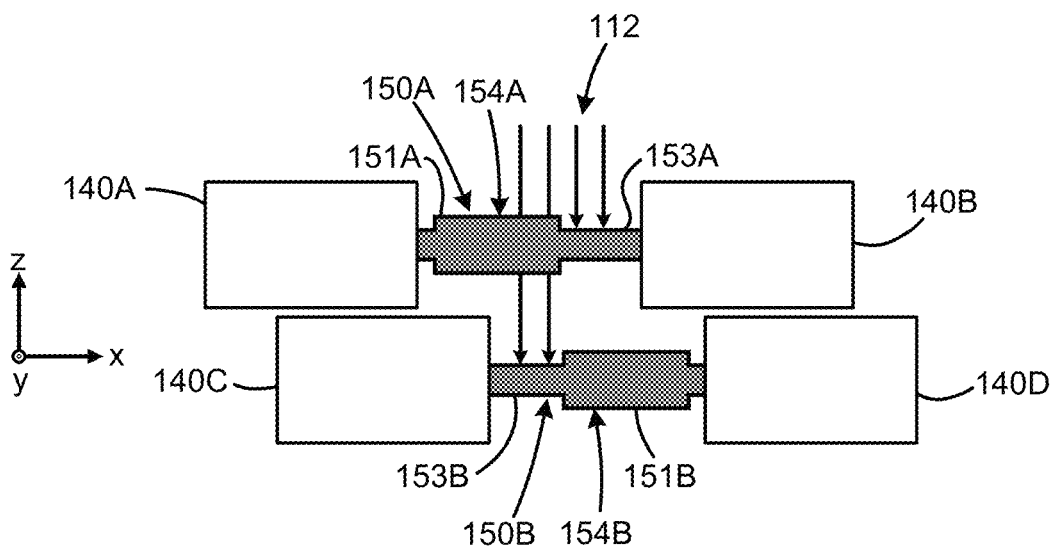

FIGS. 9A-B illustrate an example embodiment of two shuttle members and their respective actuators. The two shuttle members 150A-B and the four actuators 140A-D may constitute a shutter mechanism. FIG. 9A illustrates the shuttle members 150A-B in the open position, and FIG. 9B illustrates the shuttle members 150A-B in the closed position. The upper shuttle member 150A is moved by the two upper actuators 140A-B, and the lower shuttle member 150B is moved by the two lower actuators 140C-D. When the shuttle members 150A-B are in the open position, as shown in FIG. 9A, their windows 154A-B are aligned such that X-ray beams 112 (or other beams of light) can pass through both windows 154A-B.

When the shuttle members 150A-B are in the closed position, as shown in FIG. 9B, their windows 154A-B are offset such that no X-ray beams 112 (or other beams of light) can pass through both windows 154A-B. Instead, the X-ray beams 112 (or other beams of light) are blocked by either the opaque portion 153A of the upper shuttle member 150A or the opaque portion 153B of the lower shuttle member 150B.

Also, in the embodiment in FIG. 9A, to move between the open and closed positions, each of the shuttle members 150A-B needs to move less distance (e.g., approximately half the distance) than a shuttle member, in an embodiment that includes only one shuttle member, needs to move in order to move between the open and closed positions.

The scope of the claims is not limited to the above-described embodiments and includes various modifications and equivalent arrangements.

The invention claimed is:

1. A shutter device comprising:
a shuttle member, wherein the shuttle member includes a body, wherein the body includes an opening that extends through the body, and wherein at least part of the shuttle member is radiopaque;
a first actuator; and
a second actuator,
wherein the shuttle member is suspended from the first actuator and the second actuator and between the first actuator and the second actuator,
wherein the first actuator and the second actuator are positioned on opposite sides of the shuttle member,
wherein the first actuator is configured to move the shuttle member in a first direction, and
wherein the second actuator is configured to move the shuttle member in a second direction that is opposite to the first direction.

2. The shutter device of claim 1, wherein the body of the shuttle member forms a perimeter that surrounds the opening that extends through the body.

3. The shutter device of claim 1,
wherein one or both of the first and second actuators are pneumatic actuators, or
wherein one or both of the first and second actuators are magnetic actuators, or
wherein one or both of the first and second actuators are hydraulic actuators, or
wherein one or both of the first and second actuators are electromechanical actuators, or
wherein one or both of the first and second actuators are electrohydraulic actuators.

4. The shutter device of claim 1,
wherein the shuttle member includes a first arm that is held by the first actuator,
wherein the shuttle member includes a second arm that is held by the second actuator,
wherein the first arm is directly joined to the body, and
wherein the second arm is directly joined to the body.

5. The shutter device of claim 4, wherein the first arm is directly held by the first actuator, and
wherein the second arm is directly held by the second actuator.

6. The shutter device of claim 1, wherein, along an axis that extends from the first actuator to the second actuator, the body of the shuttle member has a circular cross section, an elliptical cross section, or a quadrilateral cross section.

7. The shutter device of claim 1, wherein the shuttle member includes a first arm that is held by the first actuator,
wherein the shuttle member includes a second arm that is held by the second actuator, and
wherein the first arm and the second arm are fixed relative to the body such that, as the shuttle member moves between the first position and the second position, the body, the first arm, and the second arm move in unison.

8. A device comprising:
an aperture;
a shuttle member, wherein the shuttle member includes a body, wherein the shuttle member includes an opening that extends through the body, and wherein the shuttle member includes a radiopaque portion;
a first actuator; and
a second actuator,
wherein the first actuator is configured to move the shuttle member to a first location in which the opening that extends through the body is aligned with the aperture,
wherein the second actuator is configured to move the shuttle member to a second location in which the radiopaque portion is aligned with the aperture, and
wherein the shuttle member is suspended from the first actuator and the second actuator and between the first actuator and the second actuator.

9. The device of claim 8,
wherein the first actuator exerts a force in a first direction, and
wherein the second actuator exerts a force in a second direction that is opposite to the first direction.

10. The imaging device of claim 9,
wherein the shuttle member includes a first arm that is held by the first actuator,
wherein the shuttle member includes a second arm that is held by the second actuator, and
wherein the body, the first arm, and the second arm are integrally formed.

11. The device of claim 8, further comprising:
an X-ray generator,
wherein the shuttle member is located between the X-ray generator and the aperture, wherein in the first location, in which the opening that extends through the body is aligned with the aperture, X-rays that are emitted by the X-ray generator travel through the opening and through the aperture, and wherein in the second position, in which the radiopaque portion is aligned with the aperture, X-rays that are emitted by the X-ray generator are blocked from traveling through the aperture by the radiopaque portion.

12. The device of claim 8, wherein the shuttle member includes a first arm that is directly held by the first actuator, and wherein the shuttle member includes a second arm that is directly held by the second actuator.

13. The device of claim 12, wherein the first arm and the second arm are fixed relative to the body such that, as the body moves between the first location and the second location, the first arm and the second arm both move in unison with the body.

14. The device of claim 8, wherein the first actuator and the second actuator are positioned on opposite sides of the body.

15. A shuttle device comprising:

a body, wherein at least a part of the body is radiopaque;

an opening that extends through the body;

a first arm that extends away from the opening, that is directly joined to the body, and that is configured to be directly held by a first actuator; and a second arm that extends away from the opening, that is directly joined to the body, and that is configured to be directly held by a second actuator, wherein the body is rigidly joined to the first arm and is rigidly joined to the second arm such that the body, the first arm, and the second arm move in unison.

16. The shuttle device of claim 15, wherein the first arm and the second arm are located on opposite sides of the body, and wherein the body is longer on a longitudinal axis that extends from the first arm to the second arm than along an axis that is perpendicular to the longitudinal axis.

17. The shuttle device of claim 16, wherein, along the longitudinal axis, the body has a circular cross section or an elliptical cross section.

18. The shuttle device of claim 16, wherein, along the longitudinal axis, the body has a polygonal cross section.

19. The shuttle device of claim 16, wherein the body includes a hollow space that extends along a longitudinal axis.

20. The shuttle device of claim 16, wherein the axis that is perpendicular to the longitudinal axis is also perpendicular to an axis that extends through the opening, and wherein a thickness of the first arm along the axis that is perpendicular to the longitudinal axis is less than a thickness of the body along the axis that is perpendicular to the longitudinal axis.

\* \* \* \* \*